(12) United States Patent
Alshaiba Saleh Ghannam Almazrouei et al.

(10) Patent No.: US 11,944,120 B2
(45) Date of Patent: *Apr. 2, 2024

(54) ULTRASONIC MIST INHALER WITH CAPILLARY RETAINER

(71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Imad Lahoud, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 687 days.

This patent is subject to a terminal disclaimer.

(21) Appl. No.: 16/961,145

(22) PCT Filed: Dec. 15, 2019

(86) PCT No.: PCT/IB2019/060812
§ 371 (c)(1),
(2) Date: Jul. 9, 2020

(87) PCT Pub. No.: WO2021/123871
PCT Pub. Date: Jun. 24, 2021

(65) Prior Publication Data
US 2021/0195947 A1    Jul. 1, 2021

(51) Int. Cl.
*A24F 40/05* (2020.01)
*A24F 40/10* (2020.01)
(Continued)

(52) U.S. Cl.
CPC ............. *A24F 40/05* (2020.01); *A24F 40/10* (2020.01); *A24F 40/44* (2020.01); *B05B 17/0684* (2013.01); *A61M 11/005* (2013.01)

(58) Field of Classification Search
CPC .......... A24F 40/05; A24F 40/10; A24F 40/44; B05B 17/0661; B05B 17/0684;
(Continued)

(56) References Cited

U.S. PATENT DOCUMENTS 4,119,096 A   10/1978   Drews
4,334,531 A    6/1982   Reichel
(Continued)

FOREIGN PATENT DOCUMENTS

CN    101648041 A    2/2010
CN    104055225 A    9/2014
(Continued)

OTHER PUBLICATIONS

Extended European Search Report issued by the European Patent Office for the corresponding EP Application No. 22181106.0, dated Nov. 15, 2022, 10 pages.
(Continued)

*Primary Examiner* — Hae Moon Hyeon
*Assistant Examiner* — Thang H Nguyen
(74) *Attorney, Agent, or Firm* — Amedeo F. Ferraro

(57) ABSTRACT

An ultrasonic mist inhaler, including a liquid reservoir structure including a liquid chamber adapted to receive liquid to be atomized, a sonication chamber in fluid communication with the liquid chamber, a capillary material arranged between the liquid chamber and the sonication chamber, the sonication chamber including an ultrasonic oscillation component having an atomization surface, a capillary material retainer, wherein the capillary material retainer having a body surrounding the ultrasonic oscillation component, the retainer body having a radial arm extending to the atomization surface for retaining the capillary material in surface contact with the atomization surface.

13 Claims, 5 Drawing Sheets

Figure 1:
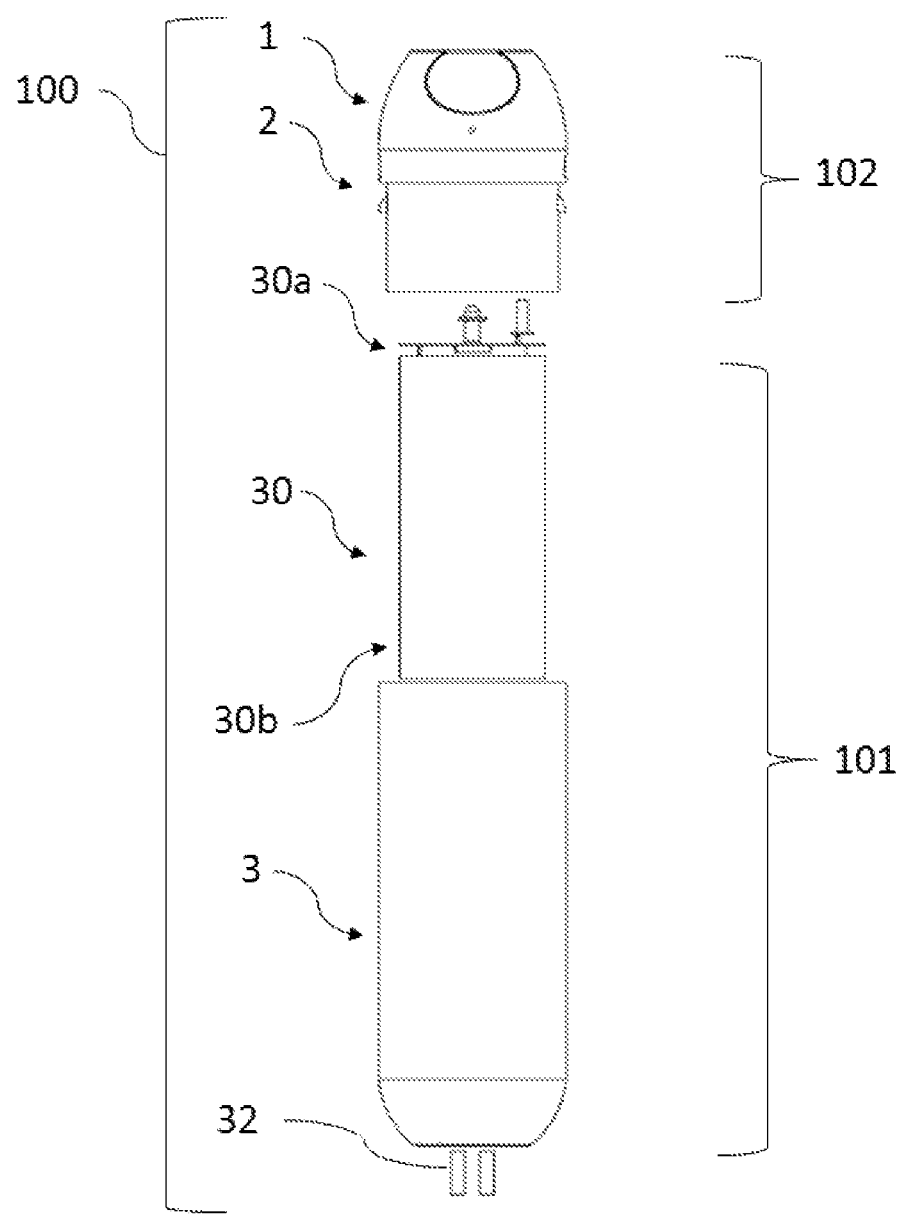

(51) Int. Cl.
  *A24F 40/44* (2020.01)
  *B05B 17/06* (2006.01)
  *A61M 11/00* (2006.01)

(58) Field of Classification Search
  CPC ............ A61M 11/005; A61M 15/0085; A61M 15/06; A61M 2016/0021; A61M 2016/0027; A61M 2202/0468; A61M 2205/0205; A61M 2205/8206
  See application file for complete search history.

(56) References Cited

U.S. PATENT DOCUMENTS

| | | | |
|---|---|---|---|
| 5,355,873 | A | 10/1994 | Del Bon |
| 5,518,179 | A | 5/1996 | Humberstone et al. |
| 5,551,416 | A | 9/1996 | Stimpson |
| 5,894,841 | A | 4/1999 | Voges |
| 6,011,345 | A | 1/2000 | Murray |
| 6,040,560 | A | 3/2000 | Fleischhauer |
| 6,402,046 | B1 | 6/2002 | Loeser |
| 6,601,581 | B1 | 8/2003 | Babaev |
| 6,679,436 | B1 | 1/2004 | Onishi |
| 8,991,722 | B2 | 3/2015 | Friend |
| 9,242,263 | B1 | 1/2016 | Copeman |
| 9,278,365 | B2 | 3/2016 | Banco |
| 9,415,412 | B2 | 8/2016 | Kawashima et al. |
| 9,687,029 | B2 | 6/2017 | Liu |
| 9,687,627 | B2 | 6/2017 | Gallem et al. |
| 9,718,078 | B1 | 8/2017 | Chau |
| 9,867,398 | B2 | 1/2018 | Guo |
| 9,980,140 | B1 | 5/2018 | Spencer |
| 10,034,495 | B2 | 7/2018 | Alarcon |
| 10,071,391 | B2 | 9/2018 | Yu |
| 10,195,368 | B2 | 2/2019 | Wang |
| 10,300,225 | B2 | 5/2019 | Terry |
| 10,327,479 | B2 | 6/2019 | Popplewell |
| 10,328,218 | B2 | 6/2019 | Reed |
| 10,412,996 | B2 | 9/2019 | Bright |
| 10,506,827 | B2 | 12/2019 | Liu |
| 10,561,803 | B2 | 2/2020 | Liu et al. |
| 10,757,971 | B2 | 9/2020 | Liu |
| 11,039,641 | B2 | 6/2021 | Liu |
| 11,207,711 | B2 | 12/2021 | Hejazi |
| 11,219,245 | B2 | 1/2022 | Liu |
| 11,278,055 | B2 | 3/2022 | Liu |
| 11,304,451 | B2 | 4/2022 | Hejazi |
| 11,431,242 | B2 | 8/2022 | Liu |
| 11,517,685 | B2 | 12/2022 | Danek |
| 11,589,609 | B2 | 2/2023 | Liu |
| 11,589,610 | B2 * | 2/2023 | Lahoud ................... A24F 40/05 |
| 11,690,963 | B2 | 7/2023 | Danek |
| 11,700,881 | B2 | 7/2023 | Liu |
| 11,744,282 | B2 | 9/2023 | Liu |
| 11,744,284 | B2 | 9/2023 | Liu |
| 11,771,137 | B2 | 10/2023 | Liu |
| 2002/0129813 | A1 | 9/2002 | Litherland |
| 2003/0192532 | A1 | 10/2003 | Hopkins |
| 2003/0209005 | A1 | 11/2003 | Fenn |
| 2006/0243277 | A1 | 11/2006 | Denyer |
| 2007/0125370 | A1 | 6/2007 | Denyer |
| 2008/0088202 | A1 | 4/2008 | Duru |
| 2008/0156320 | A1 | 7/2008 | Low |
| 2008/0164339 | A1 | 7/2008 | Duru |
| 2009/0022669 | A1 | 1/2009 | Waters |
| 2010/0084488 | A1 | 4/2010 | Mahoney, III |
| 2010/0139652 | A1 | 6/2010 | Lipp |
| 2012/0126041 | A1 | 5/2012 | Mahito et al. |
| 2013/0220315 | A1 | 8/2013 | Conley |
| 2014/0007864 | A1 | 1/2014 | Gordon et al. |
| 2014/0151457 | A1 | 6/2014 | Wilkerson |
| 2014/0261414 | A1 | 9/2014 | Weitzel |
| 2014/0270727 | A1 | 9/2014 | Ampolini |
| 2015/0054182 | A1 | 2/2015 | Kawashima et al. |
| 2015/0230522 | A1 | 8/2015 | Horn et al. |
| 2015/0231347 | A1 | 8/2015 | Gumaste et al. |
| 2015/0231660 | A1 | 8/2015 | Yu |
| 2016/0001316 | A1 | 1/2016 | Friend |
| 2016/0066619 | A1 | 3/2016 | Di Carlo |
| 2016/0089508 | A1 | 3/2016 | Smith |
| 2016/0199594 | A1 | 7/2016 | Finger |
| 2016/0206001 | A1 | 7/2016 | Eng |
| 2016/0213866 | A1 | 7/2016 | Tan |
| 2016/0279352 | A1 | 9/2016 | Wang et al. |
| 2016/0324212 | A1 | 11/2016 | Cameron |
| 2016/0338407 | A1 | 11/2016 | Kerdemelidis |
| 2017/0042242 | A1 | 2/2017 | Hon |
| 2017/0119052 | A1 | 5/2017 | Williams |
| 2017/0135411 | A1 | 5/2017 | Cameron |
| 2017/0136484 | A1 | 5/2017 | Wilkerson |
| 2017/0265521 | A1 | 9/2017 | Do |
| 2017/0281883 | A1 | 10/2017 | Li |
| 2017/0303594 | A1 | 10/2017 | Cameron |
| 2017/0368273 | A1 | 12/2017 | Rubin |
| 2018/0042306 | A1 | 2/2018 | Atkins |
| 2018/0153217 | A1 * | 6/2018 | Liu ........................ A61M 15/06 |
| 2018/0160737 | A1 | 6/2018 | Verleur |
| 2018/0161525 | A1 * | 6/2018 | Liu ..................... A61M 15/001 |
| 2018/0192702 | A1 | 7/2018 | Li |
| 2018/0269867 | A1 | 9/2018 | Terashima |
| 2018/0286207 | A1 | 10/2018 | Baker |
| 2018/0296777 | A1 | 10/2018 | Terry |
| 2018/0296778 | A1 | 10/2018 | Hacker |
| 2018/0310625 | A1 | 11/2018 | Alarcon |
| 2018/0338532 | A1 | 11/2018 | Verleur |
| 2018/0343926 | A1 | 12/2018 | Wensley |
| 2019/0056131 | A1 | 2/2019 | Warren |
| 2019/0098935 | A1 * | 4/2019 | Phan ......................... C03C 4/02 |
| 2019/0116863 | A1 | 4/2019 | Dull |
| 2019/0158938 | A1 | 5/2019 | Bowen |
| 2019/0166913 | A1 | 6/2019 | Trzecieski |
| 2019/0216135 | A1 * | 7/2019 | Guo ........................ A24F 40/44 |
| 2019/0255554 | A1 | 8/2019 | Selby et al. |
| 2019/0289914 | A1 | 9/2019 | Liu |
| 2019/0289915 | A1 | 9/2019 | Heidl |
| 2019/0289918 | A1 | 9/2019 | Hon |
| 2019/0321570 | A1 | 10/2019 | Rubin |
| 2019/0329281 | A1 | 10/2019 | Lin |
| 2019/0335580 | A1 | 10/2019 | Lin |
| 2019/0336710 | A1 | 11/2019 | Yamada |
| 2019/0373679 | A1 | 12/2019 | Fu |
| 2019/0374730 | A1 | 12/2019 | Chen |
| 2019/0387795 | A1 | 12/2019 | Fisher |
| 2020/0000143 | A1 | 1/2020 | Anderson |
| 2020/0000146 | A1 | 1/2020 | Anderson |
| 2020/0009600 | A1 | 1/2020 | Tan |
| 2020/0016344 | A1 | 1/2020 | Scheck |
| 2020/0022416 | A1 | 1/2020 | Alarcon |
| 2020/0046030 | A1 | 2/2020 | Krietzman |
| 2020/0068949 | A1 * | 3/2020 | Rasmussen ............. A24F 40/30 |
| 2020/0085100 | A1 * | 3/2020 | Hoffman ............... H05B 3/0014 |
| 2020/0120989 | A1 | 4/2020 | Danek |
| 2020/0120991 | A1 | 4/2020 | Hatton |
| 2020/0146361 | A1 | 5/2020 | Silver |
| 2020/0178598 | A1 | 6/2020 | Mitchell |
| 2020/0214349 | A1 * | 7/2020 | Liu ....................... A24F 40/485 |
| 2020/0221771 | A1 | 7/2020 | Atkins |
| 2020/0221776 | A1 | 7/2020 | Liu |
| 2020/0245692 | A1 | 8/2020 | Cameron |
| 2020/0345058 | A1 | 11/2020 | Bowen |
| 2020/0404975 | A1 | 12/2020 | Chen |
| 2021/0015957 | A1 | 1/2021 | Bush |
| 2021/0076733 | A1 | 3/2021 | Liu |
| 2021/0112858 | A1 | 4/2021 | Liu |
| 2021/0153548 | A1 | 5/2021 | Twite |
| 2021/0153549 | A1 | 5/2021 | Twite |
| 2021/0153564 | A1 | 5/2021 | Hourmand |
| 2021/0153565 | A1 | 5/2021 | Twite |
| 2021/0153566 | A1 | 5/2021 | Hourmand |
| 2021/0153567 | A1 | 5/2021 | Twite |
| 2021/0153568 | A1 | 5/2021 | Twite |
| 2021/0153569 | A1 | 5/2021 | Twite |
| 2021/0177056 | A1 | 6/2021 | Yilmaz |
| 2021/0212362 | A1 | 7/2021 | Liu |
| 2021/0378303 | A1 | 12/2021 | Liu |

(56) References Cited

U.S. PATENT DOCUMENTS

| | | | |
|---|---|---|---|
| 2021/0401061 | A1 | 12/2021 | Davis |
| 2021/0402114 | A1* | 12/2021 | Lahoud ............ A61M 15/0021 |
| 2022/0151301 | A1 | 5/2022 | Liu |
| 2022/0240589 | A1 | 8/2022 | Liu |
| 2022/0273037 | A1* | 9/2022 | Liu ........................ A24F 40/44 |
| 2022/0279857 | A1 | 9/2022 | Liu |
| 2022/0295876 | A1 | 9/2022 | Liu |
| 2022/0395023 | A1 | 12/2022 | Liu |
| 2022/0400747 | A1 | 12/2022 | Liu |
| 2023/0001107 | A1 | 1/2023 | Connolly |
| 2023/0013741 | A1 | 1/2023 | Liu |
| 2023/0020762 | A1 | 1/2023 | Liu |

FOREIGN PATENT DOCUMENTS

| | | | |
|---|---|---|---|
| CN | 204070580 | U | 1/2015 |
| CN | 105747277 | A | 7/2016 |
| CN | 105768238 | A | 7/2016 |
| CN | 105795526 | A | 7/2016 |
| CN | 205432145 | U | 8/2016 |
| CN | 106108118 | A | 11/2016 |
| CN | 205831074 | U | 12/2016 |
| CN | 106422005 | A | 2/2017 |
| CN | 205947130 | U | 2/2017 |
| CN | 206025223 | U | 3/2017 |
| CN | 206043451 | U | 3/2017 |
| CN | 206079025 | U | 4/2017 |
| CN | 206119183 | U | 4/2017 |
| CN | 206119184 | U | 4/2017 |
| CN | 106617319 | A | 5/2017 |
| CN | 206303211 | U | 7/2017 |
| CN | 206333372 | U | 7/2017 |
| CN | 107048479 | A | 8/2017 |
| CN | 206586397 | U | 10/2017 |
| CN | 206949536 | U | 2/2018 |
| CN | 105476071 | | 5/2018 |
| CN | 108283331 | A | 7/2018 |
| CN | 108355210 | A | 8/2018 |
| CN | 105876873 | B | 12/2018 |
| CN | 109619655 | A | 1/2019 |
| CN | 208434721 | U | 1/2019 |
| CN | 106108118 | B | 4/2019 |
| CN | 208837110 | U | 5/2019 |
| CN | 209060228 | U | 7/2019 |
| CN | 110150760 | A | 8/2019 |
| CN | 209255084 | U | 8/2019 |
| CN | 105876870 | B | 11/2019 |
| CN | 209900345 | U | 1/2020 |
| CN | 210076566 | U | 2/2020 |
| CN | 210225387 | | 3/2020 |
| CN | 110946315 | A | 4/2020 |
| DE | 2656370 | A1 | 6/1978 |
| DE | 2656370 | B2 | 11/1978 |
| DE | 2656370 | C3 | 7/1979 |
| DE | 100 51 792 | A1 | 5/2002 |
| DE | 10122065 | A1 | 12/2002 |
| EP | 0 258 637 | A1 | 3/1988 |
| EP | 0 295 122 | A2 | 12/1988 |
| EP | 0 258 637 | B1 | 6/1990 |
| EP | 0 442 510 | A1 | 8/1991 |
| EP | 0 442 510 | B1 | 1/1995 |
| EP | 0 516 565 | B1 | 4/1996 |
| EP | 0 824 927 | A | 2/1998 |
| EP | 0 833 695 | A1 | 4/1998 |
| EP | 0 845 220 | A1 | 6/1998 |
| EP | 0 893 071 | A1 | 1/1999 |
| EP | 0 970 627 | A1 | 1/2000 |
| EP | 1 083 952 | A2 | 3/2001 |
| EP | 1 618 803 | B1 | 12/2008 |
| EP | 3 088 007 | A1 | 11/2016 |
| EP | 3 192 381 | A1 | 7/2017 |
| EP | 3 278 678 | A1 | 2/2018 |
| EP | 3 298 912 | A1 | 3/2018 |
| EP | 3 088 007 | B1 | 11/2018 |
| EP | 3 434 118 | A1 | 1/2019 |
| EP | 3 469 927 | A1 | 4/2019 |
| EP | 3 505 098 | | 7/2019 |
| EP | 3 520 634 | A1 | 8/2019 |
| EP | 3 278 678 | B1 | 10/2019 |
| EP | 3 545 778 | A1 | 10/2019 |
| EP | 3 574 902 | A1 | 12/2019 |
| EP | 3 837 999 | A1 | 6/2021 |
| EP | 4033927 | | 11/2023 |
| FR | 3043576 | A1 | 5/2017 |
| FR | 3064502 | A1 | 10/2018 |
| GB | 1 528 391 | A | 10/1978 |
| GB | 2566766 | A | 3/2019 |
| GB | 2570439 | A | 7/2019 |
| JP | 5093575 | U | 12/1993 |
| JP | 2579614 | Y2 | 8/1998 |
| JP | 2001069963 | A | 3/2001 |
| JP | 2005-288400 | A | 10/2005 |
| JP | 2008-104966 | A | 5/2008 |
| JP | 2019-515690 | A | 6/2019 |
| JP | 2019-521671 | A | 8/2019 |
| JP | 2020535846 | A | 12/2020 |
| KR | 20120107219 | A | 10/2012 |
| KR | 10-2013-0095024 | | 8/2013 |
| WO | WO 92/21332 | A1 | 12/1992 |
| WO | WO 93/09881 | A2 | 5/1993 |
| WO | WO-99/64095 | A2 | 12/1999 |
| WO | WO-99/64095 | A3 | 12/1999 |
| WO | WO 2000/050111 | A | 8/2000 |
| WO | WO 2002/055131 | A2 | 7/2002 |
| WO | WO 02094342 | A2 | 11/2002 |
| WO | WO 2003/055486 | A | 7/2003 |
| WO | WO 2003/101454 | A | 12/2003 |
| WO | WO 2008/076717 | A1 | 6/2008 |
| WO | WO 2009/096346 | A1 | 8/2009 |
| WO | WO 2012/062600 | A1 | 5/2012 |
| WO | WO 2012/138835 | A2 | 10/2012 |
| WO | WO-2013/028934 | A1 | 2/2013 |
| WO | WO 2014/182736 | A1 | 11/2014 |
| WO | WO 2015/128499 | A1 | 3/2015 |
| WO | WO2015/084544 | A1 | 6/2015 |
| WO | WO-2015/115006 | A1 | 8/2015 |
| WO | WO 2016/010864 | A1 | 1/2016 |
| WO | WO 2016/0116386 | | 7/2016 |
| WO | WO-2016/118941 | A1 | 7/2016 |
| WO | WO-2016/175720 | A1 | 11/2016 |
| WO | WO-2016/196915 | A1 | 12/2016 |
| WO | WO-2017/076590 | A1 | 5/2017 |
| WO | WO-2017/108268 | A1 | 6/2017 |
| WO | WO 2017/143515 | A1 | 8/2017 |
| WO | WO 2017/177159 | A2 | 10/2017 |
| WO | WO 2017/197704 | A1 | 11/2017 |
| WO | WO-2017/206022 | A1 | 12/2017 |
| WO | WO 2017/206212 | A1 | 12/2017 |
| WO | WO 2017/215221 | A1 | 12/2017 |
| WO | WO 2018/000761 | A1 | 1/2018 |
| WO | WO 2018/000829 | A1 | 1/2018 |
| WO | WO 2018/023920 | A1 | 2/2018 |
| WO | WO-2018/027189 | A2 | 2/2018 |
| WO | WO 2018/032672 | A1 | 2/2018 |
| WO | WO 2018/040380 | A1 | 3/2018 |
| WO | WO-2018/041106 | A1 | 3/2018 |
| WO | WO-2018/113669 | A1 | 6/2018 |
| WO | WO 2018/115781 | A1 | 6/2018 |
| WO | WO-2018/163366 | A1 | 9/2018 |
| WO | WO 2018/188616 | A1 | 10/2018 |
| WO | WO 2018/188638 | A1 | 10/2018 |
| WO | WO-2018/211252 | A1 | 11/2018 |
| WO | WO-2018/220586 | A2 | 12/2018 |
| WO | WO-2018/220599 | A1 | 12/2018 |
| WO | WO 2019/048749 | A1 | 3/2019 |
| WO | WO-2019/052506 | A1 | 3/2019 |
| WO | WO-2019/052574 | A1 | 3/2019 |
| WO | WO 2019/069160 | A1 | 4/2019 |
| WO | WO-2019/138076 | A1 | 7/2019 |
| WO | WO-2019/198688 | A1 | 10/2019 |
| WO | WO 2019/238064 | | 12/2019 |
| WO | WO 2019/242746 | A1 | 12/2019 |
| WO | WO 2020/019030 | A1 | 1/2020 |
| WO | WO 2020/048437 | A1 | 3/2020 |

(56) References Cited

FOREIGN PATENT DOCUMENTS

| WO | WO-2020/057636 A1 | 3/2020 |
| WO | WO2020187138 A1 | 9/2020 |
| WO | WO-2020/225534 A1 | 11/2020 |
| WO | WO 2020/254862 A1 | 12/2020 |
| WO | WO-2021/036827 A1 | 3/2021 |

OTHER PUBLICATIONS

Extended Search Report issued by the European Patent Office, dated Dec. 1, 2022, 11 pages, for corresponding European Patent Application No. 1993337.8.

Reasons for Rejection with English translation, issued by the Japanese Patent Office dated Nov. 1, 2022, 5 pages, for corresponding Japanese Patent Application No. 2022-545772.

Combined Search and Examination Report dated Nov. 24, 2021, from application No. 2111261.0, 9 pages.

Combined Search and Examination Report dated Nov. 24, 2021, from application No. 2113623.9, 9 pages.

European Extended Search Report dated Jun. 22, 2021, from application No. 19870057.7, 9 pages.

Extended European Search Report dated May 26, 2021, from application No. 20214228.7, 18 pages.

Extended European Search Report dated Nov. 12, 2021, from application No. 19870060.1, 8 pages.

Extended European Search Report dated Nov. 9, 2020, from application No. 19870059.3, 7 pages.

Extended European Search Report dated Oct. 27, 2021, from application No. 19870058.5, 8 pages.

Extended European Search Report dated Sep. 15, 2020, from application No. 20168938.7, 8 pages.

International Search Report and Written Opinion dated Apr. 29, 2020, from application No. PCT/IB2019/055192, 7 pages.

International Search Report and Written Opinion dated Jun. 25, 2020, from application No. PCT/IB2019/060808, 8 pages.

International Search Report and Written Opinion dated Nov. 10, 2020, from application No. PCT/IB2019/060812, 9 pages.

International Search Report and Written Opinion dated Nov. 4, 2020, from application No. PCT/IB2019/060807, 9 pages.

International Search Report and Written Opinion dated Oct. 19, 2020, from application No. PCT/IB2019/060810, 8 pages.

International Search Report and Written Opinion dated Oct. 20, 2020, from application No. PCT/IB2019/060811, 9 pages.

International Search Report and Written Opinion dated Nov. 4, 2020, from application No. PCT/IB2019/060806, 8 pages.

\* cited by examiner

ULTRASONIC MIST INHALER WITH CAPILLARY RETAINER

CROSS-REFERENCE TO RELATED APPLICATION

This application is a U.S. national stage application under section 35 U.S.C. § 371 of International Application No. PCT/IB2019/060812, filed Dec. 15, 2019, the entire contents of which are incorporated herein in its entirety.

FIELD OF THE DISCLOSED TECHNOLOGY

The invention relates to an ultrasonic mist inhaler for atomizing a liquid by ultrasonic vibrations.

BACKGROUND

Electronic vaporizing inhalers are becoming popular among smokers who also want to avoid the tar and other harsh chemicals associated with traditional cigarettes and who wish to satisfy the craving for nicotine. Electronic vaporizing inhalers may contain liquid nicotine, which is typically a mixture of nicotine oil, a solvent, water, and often flavoring. When the user draws, or inhales, on the electronic vaporizing inhaler, the liquid nicotine is drawn into a vaporizer where it is heated into a vapor. As the user draws on the electronic vaporizing inhaler, the vapor containing the nicotine is inhaled. Such electronic vaporizing inhalers may have medical purpose.

Electronic vaporizing inhalers and other vapor inhalers typically have similar designs. Most electronic vaporizing inhalers feature a liquid nicotine reservoir with an interior membrane, such as a capillary element, typically cotton, that holds the liquid nicotine so as to prevent leaking from the reservoir. Nevertheless, these cigarettes are still prone to leaking because there is no obstacle to prevent the liquid from flowing out of the membrane and into the mouthpiece. A leaking electronic vaporizing inhaler is problematic for several reasons. As a first disadvantage, the liquid can leak into the electronic components, which can cause serious damage to the device. As a second disadvantage, the liquid can leak into the electronic vaporizing inhaler mouthpiece, and the user may inhale the unvaporized liquid.

Electronic vaporizing inhalers are also known for providing inconsistent doses between draws. The aforementioned leaking is one cause of inconsistent doses because the membrane may be oversaturated or undersaturated near the vaporizer. If the membrane is oversaturated, then the user may experience a stronger than desired dose of vapor, and if the membrane is undersaturated, then the user may experience a weaker than desired dose of vapor. Additionally, small changes in the strength of the user's draw may provide stronger or weaker doses. Inconsistent dosing, along with leaking, can lead to faster consumption of the vaping liquid.

Additionally, conventional electronic vaporizing inhalers tend to rely on inducing high temperatures of a metal heating component configured to heat a liquid in the e-cigarette, thus vaporizing the liquid that can be breathed in. Problems with conventional electronic vaporizing inhalers may include the possibility of burning metal and subsequent breathing in of the metal along with the burnt liquid. In addition, some may not prefer the burnt smell caused by the heated liquid.

Thus, a need exists in the art for an electronic vaporizing inhaler that is better able to withstand these disadvantages.

BRIEF SUMMARY

According to one aspect of the invention, an ultrasonic mist inhaler, comprises:

a liquid reservoir structure comprising a liquid chamber adapted to receive liquid to be atomized, a sonication chamber in fluid communication with the liquid chamber, a capillary element arranged between the liquid chamber and the sonication chamber, the sonication chamber comprising means of ultrasonic vibrations having an atomization surface, a capillary element retainer, wherein the capillary element retainer having a body surrounding the means of ultrasonic vibrations, the retainer body having an radial arm extending to the atomization surface for retaining the capillary element in surface contact with the atomization surface.

Conventional springs are used for maintaining the capillary element onto the atomization surface. Spring are made of mild steel and can rust when in contact with liquid. This can cause harmful chemicals fusing into mist.

Further, the spring can rip the surface of gauze due to sharp edges and it is difficult to assemble into the airflow channel of the inhalers and increase the height of the airflow channel from which the mist is drawn to the mouthpiece.

The arrangement of the invention allows the height of the airflow channel to be decreased. Thus, reducing the overall size of the inhaler.

The capillary retainer according to the invention prevents the use of springs.

In the ultrasonic mist inhaler, the retainer body is made in silicone.

The radial arm is flexible in order to not prevent the vibration of the means of vibrations.

The expression "means of ultrasonic vibrations" is similar to the expression "ultrasonic oscillation component" used in the patent application PCT/IB2019/055192.

In the ultrasonic mist inhaler, the capillary element retainer may be made by injection molding. Thus, it may reduce the overall cost of the inhaler.

In the ultrasonic mist inhaler, the capillary element retainer may be made of food grade plastic. Such design prevents any undesired chemical reaction with the mist.

The capillary element according to the invention allows a high absorption capacity, a high rate of absorption as well as a high fluid-retention ratio.

It was found that the inherent properties of the proposed material used for the capillarity have a significant impact on the efficient functioning of the ultrasonic mist inhaler.

Further, inherent properties of the proposed material include a good hygroscopicity while maintaining a good permeability. This allows the drawn liquid to efficiently permeate the capillary while the observed high absorption capacity allows the retention of a considerable amount of liquid thus allowing the ultrasonic mist inhaler to last for a longer time when compared with the other products available in the market.

Another significant advantage of using the bamboo fibers is the naturally occurring antimicrobial bio-agent namely "Kun" inherently present within the bamboo fiber making it antibacterial, anti-fungal and odor resistant making it suitable for medical applications.

The inherent properties have been verified using numerical analysis regarding the benefits of the bamboo fiber for sonication.

The following formulae have been tested with bamboo fibers material and others material such a cotton, paper, or other fiber strands for the use as capillary element and demonstrates that bamboo fibers have much better properties for the use in sonication:

$$C = A + \frac{T}{W_f} - \frac{1}{P_f} + (1-\alpha)\frac{V_d}{W_f}$$

wherein:

C (cc/gm of fluid/gm) is the volume per mass of the liquid absorbed divided by the dry mass of the capillary element,
A (cm$^2$) is the total surface area of the capillary element
T (cm) is the thickness of the capillary element,
$W_f$ (gm) is the mass of the dry capillary element,
$P_f$ (cc/g·sec) is the density of the dry capillary element,
$\alpha$ is the ratio of increase in volume of capillary element upon wetting to the volume of liquid diffused in the capillary element,
$V_d$ (cc) is the amount of liquid diffused in the capillary element, $$\text{Absorbent Rate}, Q = \frac{\pi r \gamma l \cos\theta}{2\eta} \cdot \left(\frac{T}{W_f} - \frac{1}{AP_f}\right)$$

Q (cc/sec) is the amount of liquid absorbed per unit time,
r (cm) is the radius of the pores within the capillary element,
$\gamma$ (N/m) is the surface tension of the liquid,
$\theta$ (degrees) is the angle of contact of the fiber,
$\eta$ (m$^2$/sec) is the viscosity of the fluid.

In the ultrasonic mist inhaler, the capillary element may be a material at least partly in bamboo fibers.

In the ultrasonic mist inhaler, the capillary element material may be 100% bamboo fiber.

Extensive testing have concluded that a 100% pure bamboo fiber is the most optimal choice for sonication.

In the ultrasonic mist inhaler, the capillary element material may be at least 75% bamboo fiber and, preferably, 25% cotton.

Capillary element from 100% pure bamboo fiber or with a high percentage of bamboo fibers demonstrates a high absorption capacity as well as improved fluid transmission making it an optimal choice for the application of the ultrasonic mist inhaler.

In the ultrasonic mist inhaler, the capillary element may have a flat shape.

In the ultrasonic mist inhaler, the capillary element may comprise a central portion and a peripheral portion.

In the ultrasonic mist inhaler, the peripheral portion may have an L-shape cross section extending down to the liquid chamber.

In the ultrasonic mist inhaler, the central portion may have a U-shape cross section on top of the means of ultrasonic vibrations.

It is noted that the expression "mist" used in the invention means the liquid is not heated as usually in traditional inhalers known from the prior art. In fact, traditional inhalers use heating elements to heat the liquid above its boiling temperature to produce a vapor, which is different from a mist.

In fact, when sonicating liquids at high intensities, the sound waves that propagate into the liquid media result in alternating high-pressure (compression) and low-pressure (rarefaction) cycles, at different rates depending on the frequency. During the low-pressure cycle, high-intensity ultrasonic waves create small vacuum bubbles or voids in the liquid. When the bubbles attain a volume at which they can no longer absorb energy, they collapse violently during a high-pressure cycle. This phenomenon is termed cavitation. During the implosion very high pressures are reached locally. At cavitation, broken capillary waves are generated, and tiny droplets break the surface tension of the liquid and are quickly released into the air, taking mist form.

The ultrasonic mist inhaler according to the invention, wherein said liquid to be received in the liquid chamber comprises 57-70% (w/w) vegetable glycerin and 30-43% (w/w) propylene glycol, said propylene glycol including nicotine and flavorings.

An ultrasonic mist inhaler or a personal ultrasonic atomizer device, comprising:

- a liquid reservoir structure comprising a liquid chamber or cartridge adapted to receive liquid to be atomized,
- a sonication chamber in fluid communication with the liquid chamber or cartridge, wherein said liquid to be received in the liquid chamber comprises 57-70% (w/w) vegetable glycerin and 30-43% (w/w) propylene glycol, said propylene glycol including nicotine and flavorings.

BRIEF DESCRIPTION OF THE DRAWINGS

Some embodiments are illustrated by way of example and not limitation in the figures of the accompanying drawings.

FIG. 1 is an exploded view of components of the ultrasonic mist inhaler according to an embodiment of the invention.

FIG. 2 is an exploded view of components of the inhaler liquid reservoir structure according to an embodiment of the invention.

FIG. 3 is a cross section view of components of the inhaler liquid reservoir structure according to FIG. 1.

FIG. 4A is an isometric view of an airflow member of the inhaler liquid reservoir structure according to FIGS. 2 and 3.

FIG. 4B is a cross section view of the airflow member shown in FIG. 4A.

FIG. 5A is a side view of a capillary element retainer according to the invention.

FIG. 5B is a top view of the capillary element retainer shown in FIG. 5A.

FIG. 5C is a cross section view of the capillary element retainer shown in FIG. 5A.

DETAILED DESCRIPTION

The foregoing summary, as well as the following detailed description of certain embodiments of the present invention, will be better understood when read in conjunction with the appended drawings.

As used herein, an element recited in the singular and preceded with the word "a" or "an" should be understood as not excluding plural of said elements, unless such exclusion is explicitly stated. Furthermore, the references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention is directed to an ultrasonic mist inhaler. The description of the invention and accompanying figures will be directed to the electronic vaporizing inhaler embodiment; however, other embodiments are envisioned, such as an inhaler for hookah, flavored liquids, medicine, and herbal supplements. Additionally, the device can be packaged to look like an object other than a cigarette. For instance, the device could resemble another smoking instrument, such as a pipe, water pipe, or slide, or the device could resemble another non-smoking related object.

Ultrasonic mist inhalers are either disposable or reusable. The term "reusable" as used herein implies that the energy storage device is rechargeable or replaceable or that the liquid is able to be replenished either through refilling or through replacement of the liquid reservoir structure. Alternatively, in some embodiments reusable electronic device is both rechargeable and the liquid can be replenished. A disposable embodiment will be described first, followed by a description of a reusable embodiment.

Conventional electronic vaporizing inhalers tend to rely on inducing high temperatures of a metal component configured to heat a liquid in the inhaler, thus vaporizing the liquid that can be breathed in. The liquid typically contains nicotine and flavorings blended into a solution of propylene glycol (PG) and vegetable glycerin (VG), which is vaporized via a heating component at high temperatures. Problems with conventional inhaler may include the possibility of burning metal and subsequent breathing in of the metal along with the burnt liquid. In addition, some may not prefer the burnt smell or taste caused by the heated liquid.

In contrast, aspects of the present disclosure include an ultrasonic mist inhaler that atomizes the liquid through ultrasonic vibrations, which produces micro water bubbles in the liquid. When the bubbles come into contact with ambient air, water droplets of about 0.25 to 0.5 microns spray into the air, thereby generating micro-droplets that can be absorbed through breathing, similar to breathing in a mist.

No heating elements are involved, thereby leading to no burnt elements and reducing second-hand smoke effects.

FIG. 1 to FIG. 4 illustrates an embodiment of an ultrasonic inhaler comprising a capillary element mechanical spring retainer 9 for retaining the capillary element 7 in surface contact with the atomization surface 5.

FIG. 1 depicts a disposable ultrasonic mist inhaler embodiment 100 of the invention. As can be seen in FIG. 1, the ultrasonic mist inhaler 100 has a cylindrical body with a relatively long length as compared to the diameter. In terms of shape and appearance, the ultrasonic mist inhaler 100 is designed to mimic the look of a typical cigarette. For instance, the inhaler can feature a first portion 101 that primarily simulates the tobacco rod portion of a cigarette and a second portion 102 that primarily simulates a filter. In the disposable embodiment of the invented device, the first portion and second portion are regions of a single, but-separable device. The designation of a first portion 101 and a second portion 102 is used to conveniently differentiate the components that are primarily contained in each portion.

As can be seen in FIG. 1, the ultrasonic mist inhaler comprises a mouthpiece 1, a liquid reservoir structure 2 and a casing 3. The first portion 101 comprises the casing 3 and the second portion 102 comprises the mouthpiece 1 and the reservoir structure 2.

The first portion 101 contains the power supply energy.

An electrical storage device 30 powers the ultrasonic mist inhaler 100. The electrical storage device 30 can be a battery, including but not limited to a lithium-ion, alkaline, zinc-carbon, nickel-metal hydride, or nickel-cadmium battery; a super capacitor; or a combination thereof. In the disposable embodiment, the electrical storage device 30 is not rechargeable, but, in the reusable embodiment, the electrical storage device 30 would be selected for its ability to recharge. In the disposable embodiment, the electrical storage device 30 is primarily selected to deliver a constant voltage over the life of the inhaler 100. Otherwise, the performance of the inhaler would degrade over time. Preferred electrical storage devices that are able to provide a consistent voltage output over the life of the device include lithium-ion and lithium polymer batteries.

The electrical storage device 30 has a first end **30*a* that generally corresponds to a positive terminal and a second end 30*b* that generally corresponds to a negative terminal. The negative terminal is extending to the first end 30*a***.

Because the electrical storage device 30 is located in the first portion 101 and the liquid reservoir structure 2 is located in the second portion 102, the joint needs to provide electrical communication between those components. In the present invention, electrical communication is established using at least an electrode or probe that is compressed together when the first portion 101 is tightened into the second portion 102.

In order for this embodiment to be reusable, the electrical storage device 30 is rechargeable. The casing 3 contains a charging port 32.

The integrated circuit 4 has a proximal end **4*a* and a distal end 4*b*. The positive terminal at the first end 30*a* of the electrical storage device 30 is in electrical communication with a positive lead of the flexible integrated circuit 4. The negative terminal at the second end 30*b* of the electrical storage device 30 is in electrical communication with a negative lead of the integrated circuit 4. The distal end 4*b* of the integrated circuit 4 comprise a microprocessor. The microprocessor is configured to process data from a sensor, to control a light, to direct current flow to means of ultrasonic vibrations 5 in the second portion 102**, and to terminate current flow after a preprogrammed amount of time.

The sensor detects when the ultrasonic mist inhaler 100 is in use (when the user draws on the inhaler) and activates the microprocessor. The sensor can be selected to detect changes in pressure, air flow, or vibration. In a preferred embodiment, the sensor is a pressure sensor. In the digital embodiment, the sensor takes continuous readings which in turn requires the digital sensor to continuously draw current, but the amount is small and overall battery life would be negligibly affected.

Additionally, the integrated circuit 4 may comprise a H bridge, preferably formed by 4 MOSFETs to convert a direct current into an alternate current at high frequency.

Referring to FIG. 2 and FIG. 3, illustrations of a liquid reservoir structure 2 according to an embodiment are shown. The liquid reservoir structure 2 comprises a liquid chamber 21 adapted to receive liquid to be atomized and a sonication chamber 22 in fluid communication with the liquid chamber 21.

In the embodiment shown, the liquid reservoir structure 2 comprises an inhalation channel 20 providing an air passage from the sonication chamber 22 toward the surroundings.

As an example of sensor position, the sensor may be located in the sonication chamber 22.

The inhalation channel 20 has a frustoconical element **20*a* and an inner container 20*b***.

As depicted in FIGS. 4A and 4B, further the inhalation channel 20 has an airflow member 27 for providing air flow from the surroundings to the sonication chamber 22.

The airflow member 27 has an airflow bridge **27*a* and an airflow duct 27*b* made in one piece, the airflow bridge 27*a* having two airway openings 27*a*' forming a portion of the inhalation channel 20 and the airflow duct 27*b* extending in the sonication chamber 22 from the airflow bridge 27*a*** for providing the air flow from the surroundings to the sonication chamber.

The airflow bridge 27a cooperates with the frustoconical element 20a at the second diameter 20a2.

The airflow bridge 27a has two opposite peripheral openings 27a" providing air flow to the airflow duct 27b.

The cooperation with the airflow bridge 27a and the frustoconical element 20a is arranged so that the two opposite peripheral openings 27a" cooperate with complementary openings 20a" in the frustoconical element 20a.

The mouthpiece 1 and the frustoconical element 20a are radially spaced and an airflow chamber 28 is arranged between them.

Figure 2:
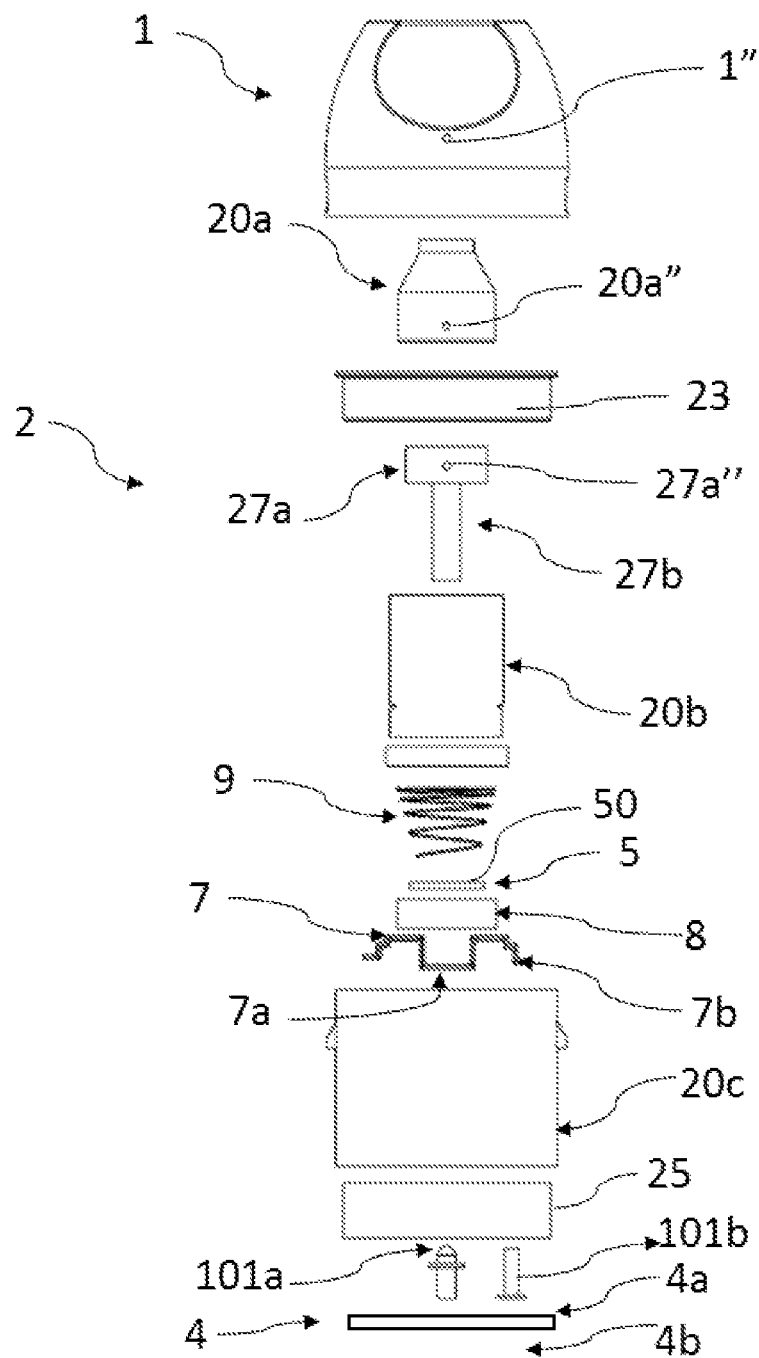

As depicted in FIGS. 1 and 2, the mouthpiece 1 has two opposite peripheral openings 1".

The peripheral openings 27a", 20a", 1" of the airflow bridge 27a, the frustoconical element 20a and the mouthpiece 1 directly supply maximum air flow to the sonication chamber 22.

The frustoconical element 20a includes an internal passage, aligned in the similar direction as the inhalation channel 20, having a first diameter 20a1 less than that of a second diameter 20a2, such that the internal passage reduces in diameter over the frustoconical element 20a.

The frustoconical element 20a is positioned in alignment with the means of ultrasonic vibrations 5 and a capillary element 7, wherein the first diameter 20a1 is linked to an inner duct 11 of the mouthpiece 1 and the second diameter 20a2 is linked to the inner container 20b.

The inner container 20b has an inner wall delimiting the sonication chamber 22 and the liquid chamber 21.

The liquid reservoir structure 2 has an outer container 20c delimiting the outer wall of the liquid chamber 21.

The inner container 20b and the outer container 20c are respectively the inner wall and the outer wall of the liquid chamber 21.

The liquid reservoir structure 2 is arranged between the mouthpiece 1 and the casing 3 and is detachable from the mouthpiece 1 and the casing 3.

The liquid reservoir structure 2 and the mouthpiece 1 or the casing 3 may include complimentary arrangements for engaging with one another; further such complimentary arrangements may include one of the following: a bayonet type arrangement; a threaded engaged type arrangement; a magnetic arrangement; or a friction fit arrangement; wherein the liquid reservoir structure 2 includes a portion of the arrangement and the mouthpiece 1 or the casing 3 includes the complimentary portion of the arrangement.

In the reusable embodiment, the components are substantially the same. The differences in the reusable embodiment vis-a-vis the disposable embodiment are the accommodations made to replace the liquid reservoir structure 2.

Figure 3:
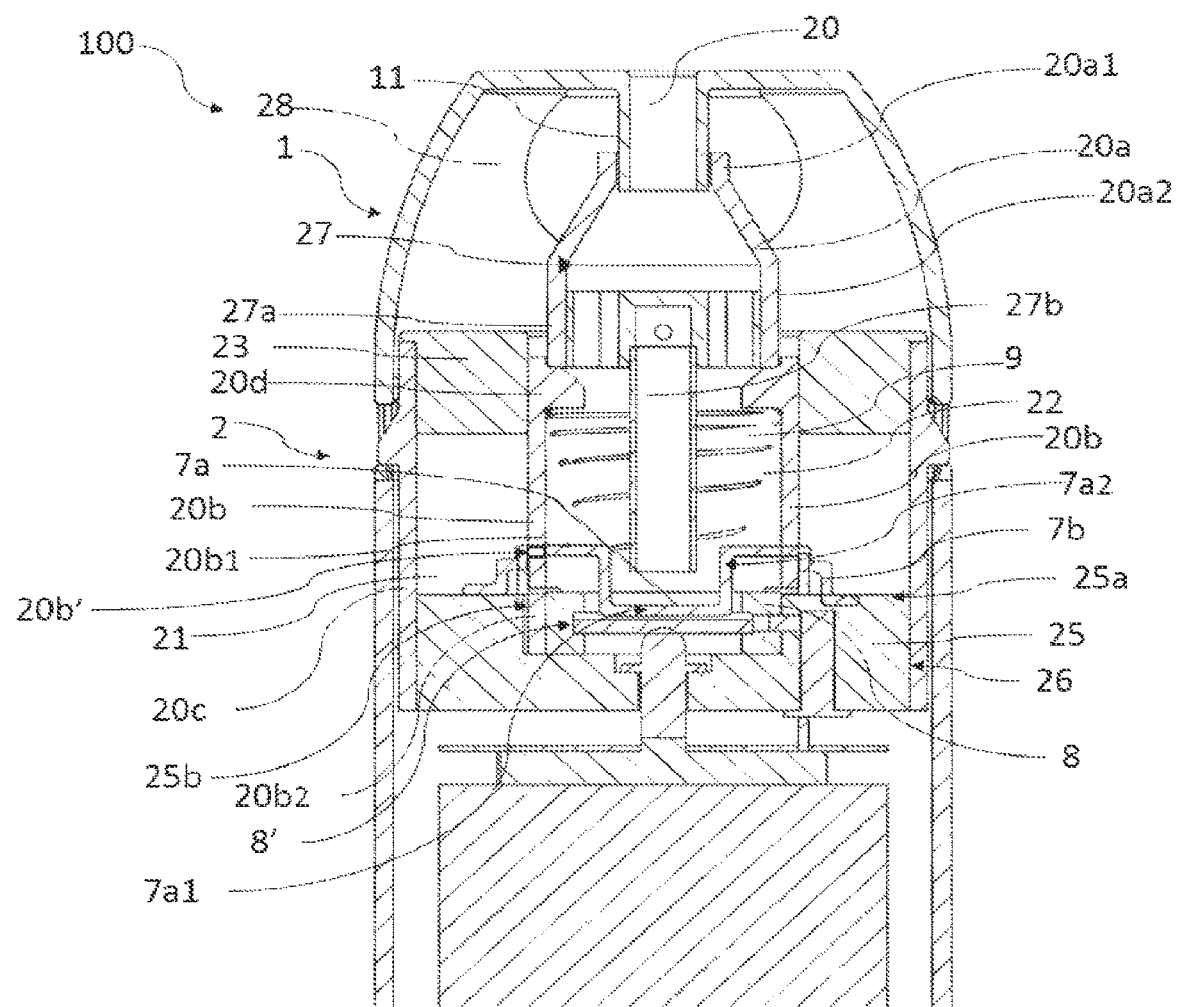
Figures 4A, 4B:
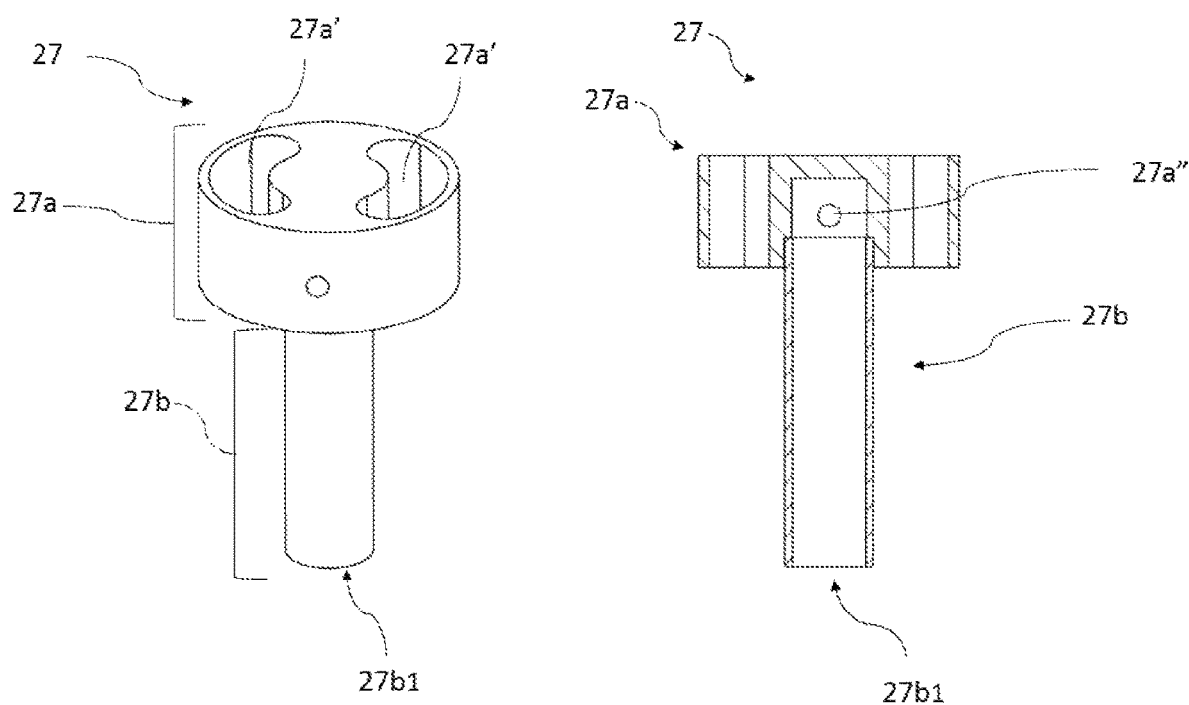

As shown in FIG. 3, the liquid chamber 21 has a top wall 23 and a bottom wall 25 closing the inner container 20b and the outer container 20c of the liquid chamber 21.

The capillary element 7 is arranged between a first section 20b1 and a second section 20b2 of the inner container 20b.

The capillary element 7 has a flat shape extending from the sonication chamber to the liquid chamber.

As depicted in FIG. 2 or 3, the capillary element 7 comprises a central portion 7a in U-shape and a peripheral portion 7b in L-shape.

The L-shape portion 7b extends into the liquid chamber 21 on the inner container 20b and along the bottom wall 25.

The U-shape portion 7a is contained into the sonication chamber 21. The U-shape portion 7a on the inner container 20b and along the bottom wall 25.

In the ultrasonic mist inhaler, the U-shape portion 7a has an inner portion 7a1 and an outer portion 7a2, the inner portion 7a1 being in surface contact with an atomization surface 50 of the means of ultrasonic vibrations 5 and the outer portion 7a2 being not in surface contact with the means of ultrasonic vibrations 5.

The bottom wall 25 of the liquid chamber 21 is a bottom plate 25 closing the liquid chamber 21 and the sonication chamber 22. The bottom plate 25 is sealed, thus preventing leakage of liquid from the sonication chamber 22 to the casing 3.

The bottom plate 25 has an upper surface 25a having a recess 25b on which is inserted an elastic member 8. The means of ultrasonic vibrations 5 are supported by the elastic member 8. The elastic member 8 is formed from an annular plate-shaped rubber having an inner hole 8' wherein a groove is designed for maintaining the means of ultrasonic vibrations 5.

The top wall 23 of the liquid chamber 21 is a cap 23 closing the liquid chamber 23.

The top wall 23 has a top surface 23 representing the maximum level of the liquid that the liquid chamber 21 may contain and the bottom surface 25 representing the minimum level of the liquid in the liquid chamber 21.

The top wall 23 is sealed, thus preventing leakage of liquid from the liquid chamber 21 to the mouthpiece 1.

The top wall 23 and the bottom wall 25 are fixed to the liquid reservoir structure 2 by means of fixation such as screws, glue or friction.

As depicted in FIG. 3, the elastic member 8 is in line contact with the means of ultrasonic vibrations 5 and prevents contact between the means of ultrasonic vibrations 5 and the inhaler walls, suppression of vibrations of the liquid reservoir structure are more effectively prevented. Thus, fine particles of the liquid atomized by the atomizing member can be sprayed farther.

As depicted in FIG. 3, the inner container 20b has openings 20b' between the first section 20b1 and the second section 20b2 from which the capillary element 7 is extending from the sonication chamber 21. The capillary element 7 absorbs liquid from the liquid chamber 21 through the apertures 20b'. The capillary element 7 is a wick. The capillary element 7 transports liquid to the sonication chamber 22 via capillary action. Preferably the capillary element 7 is made of bamboo fibers. Preferably, the capillary element 7 may be of a thickness between 0.27 mm and 0.32 mm and, preferably, has a density between 38 g/m$^2$ and 48 g/m$^2$.

As can be seen in FIG. 3, the means of ultrasonic vibrations 5 are disposed directly below the capillary element 7.

The means of ultrasonic vibrations 5 may be a transducer. For example, the means of ultrasonic vibrations 5 may be a piezoelectric transducer, preferably designed in a circular plate-shape. The material of the piezoelectric transducer is preferably in ceramic.

A variety of transducer materials can also be used for the means of ultrasonic vibrations 5.

The end of the airflow duct 27b1 faces the means of ultrasonic vibrations 5. The means of ultrasonic vibrations 5 are in electrical communication with electrical contactors 101a, 101b. It is noted that, the distal end 4b of the integrated circuit 4 has an inner electrode and an outer electrode. The inner electrode contacts the first electrical contact 101a which is a spring contact probe, and the outer electrode contacts the second electrical contact 101b which is a side pin. Via the integrated circuit 4, the first electrical contact 101a is in electrical communication with the positive terminal of the electrical storage device 30 by way of the microprocessor, while the second electrical contact 101b is in electrical communication with the negative terminal of the electrical storage device 30.

The electrical contacts 101a, 101b crossed the bottom plate 25. The bottom plate 25 is designed to be received inside the perimeter wall 26 of the liquid reservoir structure 2. The bottom plate 25 rests on complementary ridges, thereby creating the liquid chamber 21 and sonication chamber 22.

The inner container 20b comprises a circular inner slot 20d on which a capillary element mechanical spring retainer 9 is applied.

By pushing the central portion 7a1 onto the means of ultrasonic vibrations 5, the mechanical spring 9 ensures a contact surface between them.

The liquid reservoir structure 2 and the bottom plate 25 can be made using a variety of thermoplastic materials.

When the user draws on the ultrasonic mist inhaler 100, an air flow is drawn from the peripheral openings 1" and penetrates the airflow chamber 28, passes the peripheral openings 27a" of the airflow bridge 27a and the frustoconical element 20a and flows down into the sonication chamber 22 via the airflow duct 27b directly onto the capillary element 7. At the same time, the liquid is drawn from the reservoir chamber 21 by capillarity, through the plurality of apertures 20b', and into the capillary element 7. The capillary element 7 brings the liquid into contact with the means of ultrasonic vibrations 5 of the inhaler 100. The user's draw also causes the pressure sensor to activate the integrated circuit 4, which directs current to the means of ultrasonic vibrations 5. Thus, when the user draws on the mouthpiece 1 of the inhaler 100, two actions happen at the same time. Firstly, the sensor activates the integrated circuit 4, which triggers the means of ultrasonic vibrations 5 to begin vibrating. Secondly, the draw reduces the pressure outside the reservoir chamber 21 such that flow of the liquid through the apertures 20b' begins, which saturates the capillary element 7. The capillary element 7 transports the liquid to the means of ultrasonic vibrations 5, which causes bubbles to form in a capillary channel by the means of ultrasonic vibrations 5 and mist the liquid. Then, the mist liquid is drawn by the user.

The ultrasonic mist inhaler 100 of the present disclosures is a more powerful version of current portable medical nebulizers, in the shape and size of current e-cigarettes and with a particular structure for effective vaporization. It is a healthier alternative to cigarettes and current e-cigarettes products.

The ultrasonic mist inhaler 100 of the present disclosures has particular applicability for those who use electronic inhalers as a means to quit smoking and reduce their nicotine dependency. The ultrasonic mist inhaler 100 provides a way to gradually taper the dose of nicotine.

Figures 5A, 5B, 5C:
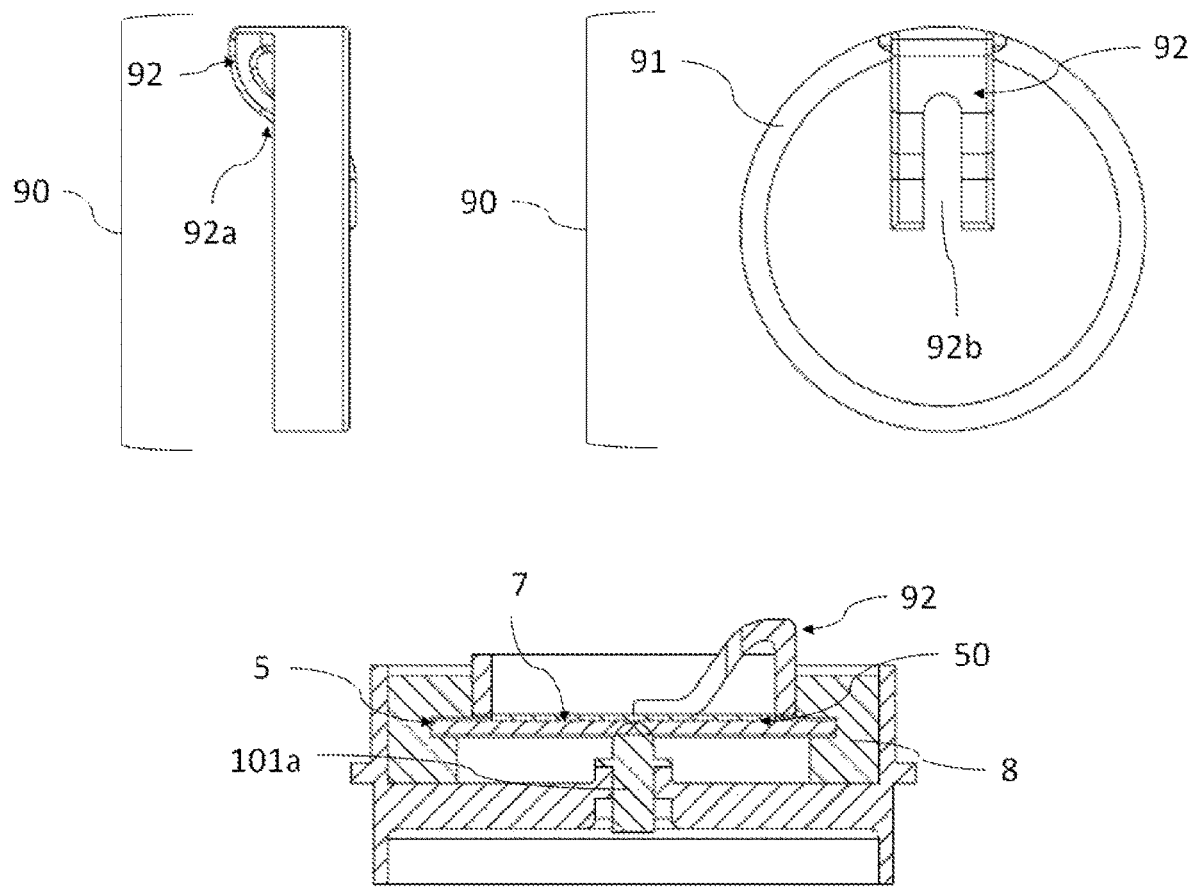

A depicted in FIGS. 5A and 5B, a capillary element retainer 90 according to the invention is shown.

The capillary element retainer 90 has a circular body 91 surrounding the means of ultrasonic vibrations 5, the retainer body 91 has an radial arm 92 extending to the atomization surface for retaining the capillary element 7 in surface contact with the atomization surface 50.

The radial arm 92 has a curved portion 92a extending inner the body 91.

The radial arm 92 has a flat portion 92b parallel to the capillary element 7.

The flat portion 92b is in fork shape. The fork shape 92b minimizes the surface contact between the capillary element 7 and the retainer 90.

The elastic element 8 surrounds the capillary element retainer 90.

Other embodiments of the invented ultrasonic mist inhaler 100 are easily envisioned, including medicinal delivery devices.

It is to be understood that the above description is intended to be illustrative, and not restrictive. For example, the above-described embodiments may be used in combination with each other. In addition, many modifications may be made to adapt a particular situation or material to the teachings of the invention without departing from its scope.

The invention claimed is:

1. An ultrasonic mist inhaler, comprising:
   a liquid reservoir structure comprising a liquid chamber adapted to receive a liquid to be atomized,
   a sonication chamber in fluid communication with the liquid chamber,
   a capillary material arranged between the liquid chamber and the sonication chamber to carry the liquid from the liquid chamber to the sonication chamber,
   an ultrasonic oscillation component in the sonication chamber, the ultrasonic oscillation component having an atomization surface, and
   a capillary material retainer; the capillary material retainer having a retainer body surrounding the atomization surface of the ultrasonic oscillation component, the retainer body having a radial arm which comprises a curved portion extending to the atomization surface and a flat portion parallel to the capillary material for retaining the capillary material in surface contact with the atomization surface, the flat portion having a fork shape which minimizes surface contact between the capillary material and the capillary material retainer, the radial arm being flexible in order to not prevent the ultrasonic oscillation component from vibrating to atomize the liquid carried by the capillary material.

2. The ultrasonic mist inhaler according to claim 1, wherein the retainer body is made of silicone.

3. The ultrasonic mist inhaler according to claim 1, wherein the capillary material retainer is made by injection molding.

4. The ultrasonic mist inhaler according to claim 1, wherein the capillary material retainer is made of food grade plastic.

5. The ultrasonic mist inhaler according to claim 1, wherein the capillary material is at least partly in bamboo fibers.

6. The ultrasonic mist inhaler according to claim 1, wherein the capillary material is 100% bamboo fiber.

7. The ultrasonic mist inhaler according to claim 1, wherein the capillary material is at least 75% bamboo fiber and, preferably, 25% cotton.

8. The ultrasonic mist inhaler according to claim 7, wherein the capillary material is of a thickness between 0.27 mm and 0.32 mm and, preferably, has a density of 38-48 g/m$^2$.

9. The ultrasonic mist inhaler according to claim 1, wherein the capillary material has a flat shape.

10. The ultrasonic mist inhaler according to claim 1, wherein the capillary material comprises a central portion and a peripheral portion.

11. The ultrasonic mist inhaler according claim 10, wherein the peripheral portion has an L-shape cross section extending down to the liquid chamber.

12. The ultrasonic mist inhaler according to claim 10, wherein the central portion has a U-shape cross section extending on top of the ultrasonic oscillation component.

13. The ultrasonic mist inhaler according to claim 1, wherein the liquid chamber receives the liquid which comprises 57-70% (w/w) vegetable glycerin and 30-43% (w/w) propylene glycol, nicotine, and flavorings.

* * * * *